United States Patent [19]

Spaeth et al.

[11] Patent Number: 5,224,930
[45] Date of Patent: Jul. 6, 1993

[54] TROCAR SYSTEM FOR FACILITATING PASSAGE OF INSTRUMENTS INTO A BODY CAVITY THROUGH A MINIMAL ACCESS INCISION

[75] Inventors: Edmund E. Spaeth, Orange; Alexander S. Borsanyi, Newport Beach; Alex Bowie, Irvine; John T. Sorensen, Costa Mesa, all of Calif.

[73] Assignee: EndoMedix Corporation, Irvine, Calif.

[21] Appl. No.: 836,080

[22] Filed: Feb. 14, 1992

Related U.S. Application Data

[63] Continuation-in-part of Ser. No. 639,494, Jan. 9, 1991, and a continuation-in-part of Ser. No. 779,443, Oct. 18, 1991.

[51] Int. Cl.$^5$ ............................................. A61B 17/34
[52] U.S. Cl. ........................................ 604/33; 606/128; 606/167; 606/170; 606/185; 604/156; 604/164; 604/169; 604/264; 604/272
[58] Field of Search ............... 128/207.29; 606/1, 167, 606/128, 184–186, 170; 604/21, 23, 26, 33, 43–45, 93, 158, 115, 161–163, 164, 167, 169, 171, 264, 272, 156

[56] References Cited

U.S. PATENT DOCUMENTS

| | | | |
|---|---|---|---|
| 4,112,932 | 9/1978 | Chiulli | 604/264 |
| 4,191,191 | 3/1980 | Auburn | 604/164 |
| 4,924,851 | 5/1990 | Ognier et al. | 604/264 |
| 5,037,379 | 8/1991 | Clayman et al. | 600/37 |
| 5,057,082 | 10/1991 | Burchette | 604/272 |
| 5,112,321 | 5/1992 | Hiltebrandt | 604/264 |
| 5,114,408 | 5/1992 | Fleischaker et al. | 604/167 |
| 5,129,885 | 7/1992 | Green et al. | 604/164 |

*Primary Examiner*—Stephen C. Pellegrino
*Assistant Examiner*—Glenn Dawson
*Attorney, Agent, or Firm*—Robert D. Buyan

[57] ABSTRACT

Devices and a system for passing instruments into a body cavity and/or for containing, manipulating, treating and removing matter from the body cavity, through a minimal access incision typically no greater than 1 cm in length. In one embodiment, the device of the invention includes an upper valving member with a plurality of interchangeable lower trocar members such as a) a short trocar member of 0.5-0.3 inches in length, b) a long trocar member greater than 3.0 inches in length and/or c) a trocar member having a protective cage disposed about its distal end attachable thereto. The lower trocar members are insertable into the body cavity. Further, in accordance with the system of the present invention, various instruments are independently insertable through the upper valving member and lower trocar portions of the device to perform various functions. The instruments which are independently insertable through the upper valving portion and lower trocar portions of the device include (a) a piercing stylet, (b) a tissue containment sac and/or containment sac introducer device and (c) a debulking or morcellizing instrument.

7 Claims, 4 Drawing Sheets

Fig. 5

TROCAR SYSTEM FOR FACILITATING PASSAGE OF INSTRUMENTS INTO A BODY CAVITY THROUGH A MINIMAL ACCESS INCISION

RELATED APPLICATIONS

This patent application is a continuation-in-part o both U.S. patent application Ser. No. 07/639,494 filed on Jan. 9, 1991 in the name of John Thomas Sorensen et al., entitled METHOD AND DEVICE FOR INTRACORPOREAL LIQUIDIZATION OF TISSUE AND/OR INTRACORPOREAL FRAGMENTATION OF CALCULI DURING ENDOSCOPIC SURGICAL PROCEDURES and U.S. patent application Ser. No. 07/779,443 filed on Oct. 18, 1991 in the name of Edmond E. Spaeth et al., entitled METHOD AND SYSTEM FOR ENCLOSING, MANIPULATING, DEBULKING AND REMOVING TISSUE THROUGH MINIMAL ACCESS INCISIONS, the disclosures of which are expressly incorporated herein by reference.

FIELD OF THE INVENTION

The present invention relates generally to medical equipment and, more particularly, to an improved trocar device and system for accessing a body cavity and for facilitating instrument passage, instrument manipulation, operative dissection, and removal of matter through minimal access body cavity incisions of the type commonly employed in endoscopic (e.g. laparoscopic) surgical procedures.

BACKGROUND OF THE INVENTION

The development of modern endoscopic devices has enabled surgeons to perform numerous surgical procedures within body cavities, under endoscopic visualization, without the need for large operative incisions. Such endoscopic procedures are typically performed by inserting an endoscope and the necessary surgical instrumentation through one or more small body openings or minimal access incisions of 1 cm or less.

Examples of endoscopic surgical procedures which have heretofore been performed through small body openings or minimal access incisions include intra-abdominal laparoscopic procedures such as, but not limited to, cholecystectomies, appendectomies, nephrectomies, tumor resections, fallopian tube ligations, etc.

Such laparoscopic surgical procedures are typically performed under general anesthesia. After the patient has been anesthetized, an inflation needle is initially inserted into the abdomen and carbon dioxide is passed through such inflation needle into the peritoneum to create a distended pneumoperitoneum. The peritoneum is typically insufflated to a pressure of 14-18 mm Hg. Once the distended pneumoperitoneum has been established, a primary trocar is inserted into the peritoneum through a small periumbilical incision or puncture cite. Additional tubular trocars may be inserted into the peritoneum at other sites on the abdominal midline or lateral to the midline.

Each trocar inserted into the abdomen is typically provided with a sealing or valving apparatus. Such sealing or valving apparatus operates to substantially prevent leakage from the pneumoperitoneum when the trocar is inserted into the pneumoperitoneum.

The laparoscopy trocars employed in typical laparoscopic applications range in diameter from approximately 5 mm-11 mm. Each instrument, cannula or scope to be inserted through a laparoscopy trocar is necessarily smaller in size than the inner diameter of the trocar through which it is to be inserted.

A puncturing stylet having a sharp tip is initially insertable through the lumen of the trocar such that the puncturing tip of the stylet initially extends slightly beyond the distal end of the trocar. With the puncturing stylet so positioned, the trocar is initially grasped by the operator and inserted into the peritoneum. Upon entry into the peritoneum, a specific change in resistance or a "snap" is felt by the operator, indicating that the puncturing tip of the stylet has penetrated the peritoneal membrane. After the trocar has been so inserted, the puncturing stylet is withdrawn and removed. The tubular trocar may then be utilized as an access route or passageway for inserting and removing various surgical instruments, scopes, cannulae and/or other apparatus into the peritoneal cavity Examples of surgical instruments which are insertable through the typical laparoscopy trocar include forceps, clamps, scissors, probes, flexible or rigid scopes and cutting instruments. Additionally, automated or powered devices such as electrocauteries and/or laser cutting/cauterization devices may also be passed into the peritoneum through such laparoscopy trocars for use in cutting and/or cauterizing tissues during laparoscopic surgical procedures.

Examples of other types of apparatus which are sometimes inserted through laparoscopic trocars include elongate devices for introducing and retrieving tissue containment sacs or bags, such as that described in U. S. Pat. No. 5,037,379 entitled SURGICAL TISSUE BAG AND METHOD FOR PERCUTANEOUSLY DEBULKING TISSUE, and that described in application Ser. No. 07/779,443 entitled METHOD AND SYSTEM FOR ENCLOSING, MANIPULATING, DEBULKING AND REMOVING TISSUE THROUGH MINIMAL ACCESS INCISIONS, of which this application is a continuation-in-part. Also, in some procedures, it is necessary to pass one or more devices for grinding, mulching, cutting, morcellizing or debulking tissue, stones or other matter. Such a device is disclosed in U.S. patent application Ser. No. 07/639,494 entitled METHOD AND DEVICE FOR INTRACORPOREAL LIQUIDIZATION OF TISSUE AND/OR INTRACORPOREAL FRAGMENTATION OF CALCULI DURING ENDOSCOPIC SURGICAL PROCEDURES, of which this application is a continuation-in-part.

These laparoscopy trocars employed in most laparoscopy applications are 5-15 cm penetrating length, measured from the surface of the skin.

In certain applications wherein an organ, sac, or other container is to be removed from a body cavity through a small (e.g. 1 cm) laparoscopy incision, such removal may be complicated or prevented if the matter contained within the organ, or the organ itself is too large or too bulky to pass through the small (e.g. 1 cm) incision. In such cases, it may be desirable to (a) use the first laparoscopy trocar to introduce an organ holding bag or sac into the abdominal cavity; (b) position the organ adjacent to or inside the sac such that the contents of the organ may be extracted from the organ and placed into the sac; (c) operatively incise the organ and place the contents of the organ into the sac; (d) externalize the first laparoscopy trocar, the sao inserting introducer, and the organ containing sac; (e) introduce a second, shorter (e.g. 3-8 cm in length) trocar into the organ-containing sac; (f) insert one or more instruments into the holding bag or sac through the second trocar to attempt to crush or remove the offending material therefrom; and, if unsuccessful, (g) remove the second shorter trocar and insert an elongated instrument into the organ holding bag to grind, pulverize, debulk, morcellize, or otherwise treat the material contained therein to facilitate removal of such material and subsequent passage of the holding bag through the small (e.g. 1 cm) incision. Thus, in such applications, it may be necessary to separately utilize one (1) long trocar, one (1) holding bag and insertion device, one (1) short trocar and one (1) elongate cutting instrument to effect final removal of the organ sao or container. Accordingly, there exists a need in the art for an improved laparoscopy trocar device having a single upper valving member with multiple interchangeable lower trocar and/or debulking aspiration portions attachable to the single upper valving assembly. Additionally, there exists a need for a complete laparoscopy system whereby the device of the foregoing character may be intermittently utilized in connection with (a) a peritoneum penetrating stylet; (b) an intraperitoneal containment sac and insertion device; (c) various forceps and other standard hand instruments; and (d) a pneumatic, electric or mechanical debulking/aspiration device.

SUMMARY OF THE INVENTION

The present invention comprises a device and system for passing instruments into a body cavity and/or for containing, manipulating, treating and removing matter from the body cavity, through a minimal access incision, typically no greater than 1 cm in length.

In accordance with the invention, there is provided a device comprising (a) an upper valving assembly and (b) a plurality of interchangeable lower trocar portions. Each lower trocar portion is insertable into the body cavity through a minimal access incision or through a standard laparoscopic portal.

In a presently preferred embodiment, the interchangeable lower trocar portions of the device comprise (a) a relatively long trocar, (b) a relatively short trocar and (c) a trocar having a protective cage assembly at its distal tip for use with a rotary debulking instrument of the type described in U.S. patent application Ser. No. 07/639,494, of which this application is a continuation in part.

The system of the present invention further comprises various instruments and devices which are insertable through the upper valving assembly and interchangeable lower trocar portions of the above-described device. In a preferred embodiment, the instruments which are insertable through the upper valving assembly and the interchangeable lower trocar portions of the device include (a) a piercing stylet, (b) a containment bag and/or containment bag introducing device and (c) a debulking or morsellizing instrument.

Further aspects, advantages and objectives of the invention will be apparent to those skilled in the art upon reading and understanding of the following detailed description and the accompanying drawings.

BRIEF DESCRIPTION OF THE DRAWINGS

FIG. 4a is a perspective view of a device of the present invention having a relatively long lower trocar member attached to the upper valving assembly and showing (a) a piercing stylet and (b) a containment bag introducing device, both of which are alternately insertable through the embodiment shown in FIG. 4a.

FIG. 4b is a perspective showing of a device of the present invention wherein a relatively short lower trocar member is attached to the upper valving assembly and having a hand operable forceps instrument insertable through the device of FIG. 4b.

FIG. 4c is a perspective showing of a device of the present invention wherein the upper valving assembly is attached to a lower trocar member which incorporates a protective cage at its distal tip, having an elongate rotary debulking instrument shown in relation thereto as an example of the type of instrument insertable through the embodiment shown in FIG. 4c.

DETAILED DESCRIPTION OF THE PREFERRED EMBODIMENTS

Figure 3:
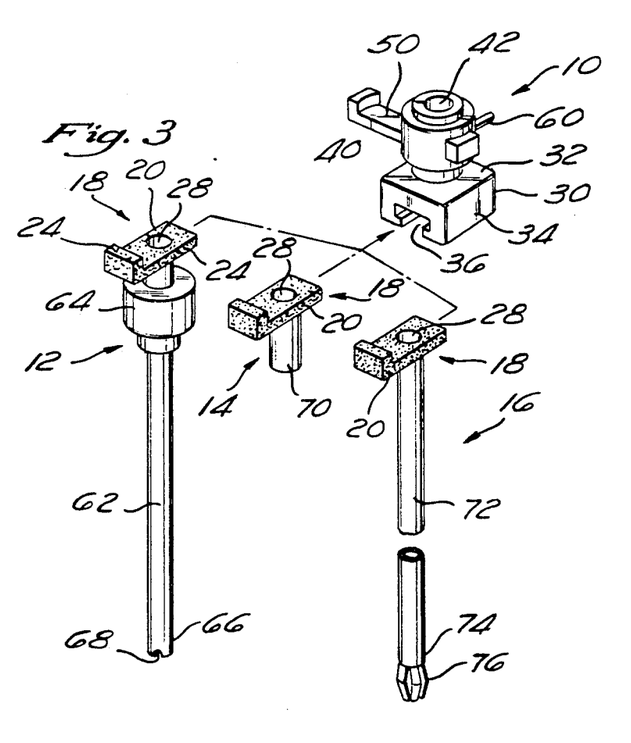
FIG. 3 is a perspective view of a device of the present invention comprising (a) a single upper valving assembly and (b) three (3) optional lower trocar members attachable to said upper valving assembly.

Referring now to the drawings wherein the showings are for purposes of illustrating preferred embodiments of the present invention only, and not for purposes of limiting the same, FIG. 3 perspectively illustrates an upper valving assembly 10 of the present invention and three differently configured lower trocar members 12, 14 and 16 which are alternately usable in conjunction with the upper valving assembly 10. Importantly, to facilitate the interchangeability of the trocar members into the upper valving assembly 10, the first trocar member 12, second trocar member 14 and third trocar member 16 each include identically configured head portions 18.

Figures 1, 2:
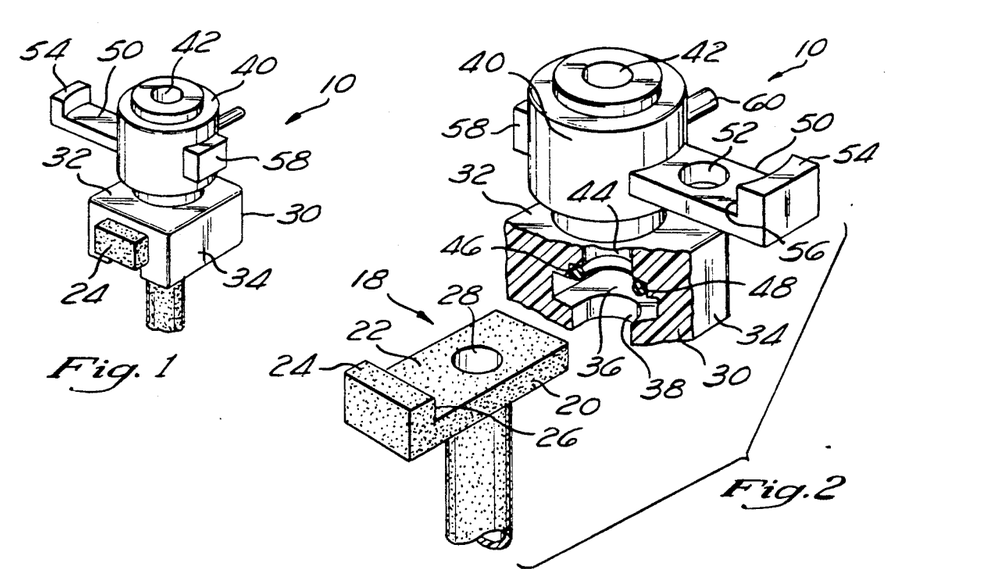
FIG. 1 is a perspective view of the upper valving assembly portion of a device of the present invention attached to one alternative lower trocar member usable in connection with such upper valving assembly.
FIG. 2 is an enlarged exploded/partial cutaway view of the portion of the device shown in FIG. 1.

Referring now to FIGS. 2 and 3, each of the head portions 18 comprises a generally rectangular base member 20 having a planar upper surface 22 and defining a pair of longitudinal sides and a pair lateral sides. Formed along one of the lateral sides of base member 20 and extending perpendicularly from upper surface 22 is rectangular extension 24 defining an inner surface 26. Additionally, disposed within the upper surface 22 of base member 20 and extending therethrough is an aperture 28, the use of which will be explained in greater detail below.

Upper valving assembly 10 generally comprises a housing 30 having a generally square configuration and defining a top surface 32 and two opposed pairs of side surfaces 34. Disposed within the housing 30 is a generally T-shaped slot 36 having an upper portion extending through the housing 30 between a pair of the opposed side surfaces 34, and a lower portion extending partially through the housing 30 and terminating at an arcuate surface 38. Importantly, the width of the upper portion of the slot 36 is substantially equal to the width, i.e. length of a lateral side, of the base member 20. Additionally, the height of the upper portion of the slot 36 is substantially equal to the height of the base member 20.

Upper valving assembly 10 further comprises a secondary cylindrical housing 40 attached to and extending upwardly from the top surface 32 of housing 30. Extending axially through the cylindrical housing 40 is an aperture 42. As best seen in FIG. 2, aperture 42 is placed into fluid communication with the upper portion of the slot 36 via an aperture 44 disposed within the top surface 32 of housing 30. Importantly, the lower end of aperture 44 includes a notch 46 formed thereabout into which is received an O-ring 48. The use of O-ring 48 will be explained in greater detail below. Slidably received into and selectively positionable within the cylindrical housing 40 is a slide valve member 50 having an aperture 52 extending axially therethrough. Slide valve member 50 has a generally rectangular configuration and includes an arcuate extension 54 formed on and extending upwardly from a lateral edge thereof. Arcuate extension 54 defines an arcuate inner surface 56 having a configuration complimentary to the outer surface of the cylindrical housing 40. Additionally, disposed on the outer surface of the cylindrical housing 40 on the side opposite that into which the slide valve member 50 is inserted is a receiving member 58 which is adapted to receive the lateral edge of slide valve member 50 opposite that on which arcuate extension 54 is formed. The cylindrical housing 40 further includes a gas inlet port 60 extending therefrom which is in fluid communication with the aperture 42.

To attach any one of the trocar members 12, 14, 16 to the upper valving assembly 10, the lateral edge of the base member 20 opposite that on which extension 24 is formed is inserted into the end of T-shaped slot 36 which includes the open lower portion. As will be recognized, the receipt of the head portion 18 into the slot 36 is limited by the abutment of the inner surface 26 of extension 24 against a side surface 34 of housing 30 or the abutment of the tubular sheath portion of one of the three trocar members 12, 14, 16 against the arcuate surface 38 defined by the lower portion of slot 36. Additionally, when the head portion 18 is fully received into the slot 36, the lateral side of base member 20 initially inserted into slot 36 will be substantially flush with the side surface 34 of housing 30 opposite that into which head portion 18 was initially inserted. Further, when head portion 18 is fully inserted into slot 36, aperture 28 will be substantially aligned and in fluid communication with aperture 44 within housing 30 as well as aperture 42 within cylindrical housing 40. Importantly, the housing 30 is sealed against the upper surface 22 of base member 20 via the compression of O-ring 48 thereagainst. As will be recognized, the sealing of the housing 30 against base member 20 via O-ring 48 allows fluids to pass through the axially aligned apertures 42, 44 and 28 without any leakage occurring. As such, aperture 28 of base member 20 serves to place head portion 18 and hence the upper valving assembly 10 in fluid communication with the inner lumen extending through the tubular sheath portion of any of the trocar members 12, 14 or 16.

In the preferred embodiment, the passage between the upper valving assembly 10 and inner lumen of a lower trocar member sheath portion facilitated by the coaxially aligned apertures 42, 44 and 28 may be selectively opened and closed by the slide valve member 50. In this respect, the slide valve member 50 is movable between a first, closed position (shown in FIGS. 1-3) wherein the slide valve member 50 forms an obstruction between the apertures 42 and 44, and a second, open position wherein the aperture 42 is fluidly connected to the aperture 44 via the aperture 52 disposed within the slide valve member 50. When the slide valve member 50 is actuated to the open position, the aperture 52 is oriented so as to be coaxially aligned between the aperture 42 and aperture 44 via the abutment of the arcuate inner surface 56 of arcuate extension 54 against the outer surface of cylindrical housing 40. When such abutment occurs, the lateral side of valve member 50 opposite that on which arcuate extension 54 is formed is received into the receiving member 58. As will be recognized, when the slide valve member 50 is actuated to the open position, a surgical instrument may be inserted through the upper valving assembly 10 into the inner lumen of a tubular sheath portion via the apertures 42, 52, 44 and 28. The upper portion 42A of cylindrical housing 40 valving assembly 10 further includes sealing components disposed therewithin which prevents fluid from leaking from the upper valving assembly 10 when a surgical instrument is inserted therethrough.

As best seen in FIG. 3, the lower trocar members 12, 14 and 16, though having identically configured head portions 18, are structurally varied for use in different surgical applications. Particularly, first trocar member 12 includes a relatively long, tubular sheath 62 extending downwardly from the head portion 18 thereof. Separating tubular sheath 62 from head portion 18 is a cylindrical section 64. Additionally, disposed within the lower, distal tip 66 of tubular sheath 62 is a notch 68 which is used for purposes which will be explained in greater detail below. Second trocar member 14 generally comprises a relatively short, tubular sheath 70 extending downwardly from head portion 18 thereof. Finally, third trocar member 16, like first trocar member 12, generally comprises a relatively long, tubular sheath 72 extending downwardly from the head portion 18 thereof. Disposed on the lower, distal tip 74 of tubular sheath 72 is a protective cage 76, the use of which will also be explained in greater detail below. As previously specified, due to the inclusion of the commonly configured head portions 18, trocar members 12, 14 and 16 are selectively, alternately attachable to the upper valving assembly 10. It will be recognized that trocar members having configurations differing from those previously described may also be interfaced to upper valving assembly 10, with the only requirement being that such trocar member include a head portion identically configured to the head portions 18 previously described.

Figures 4A, 4B, 4C:
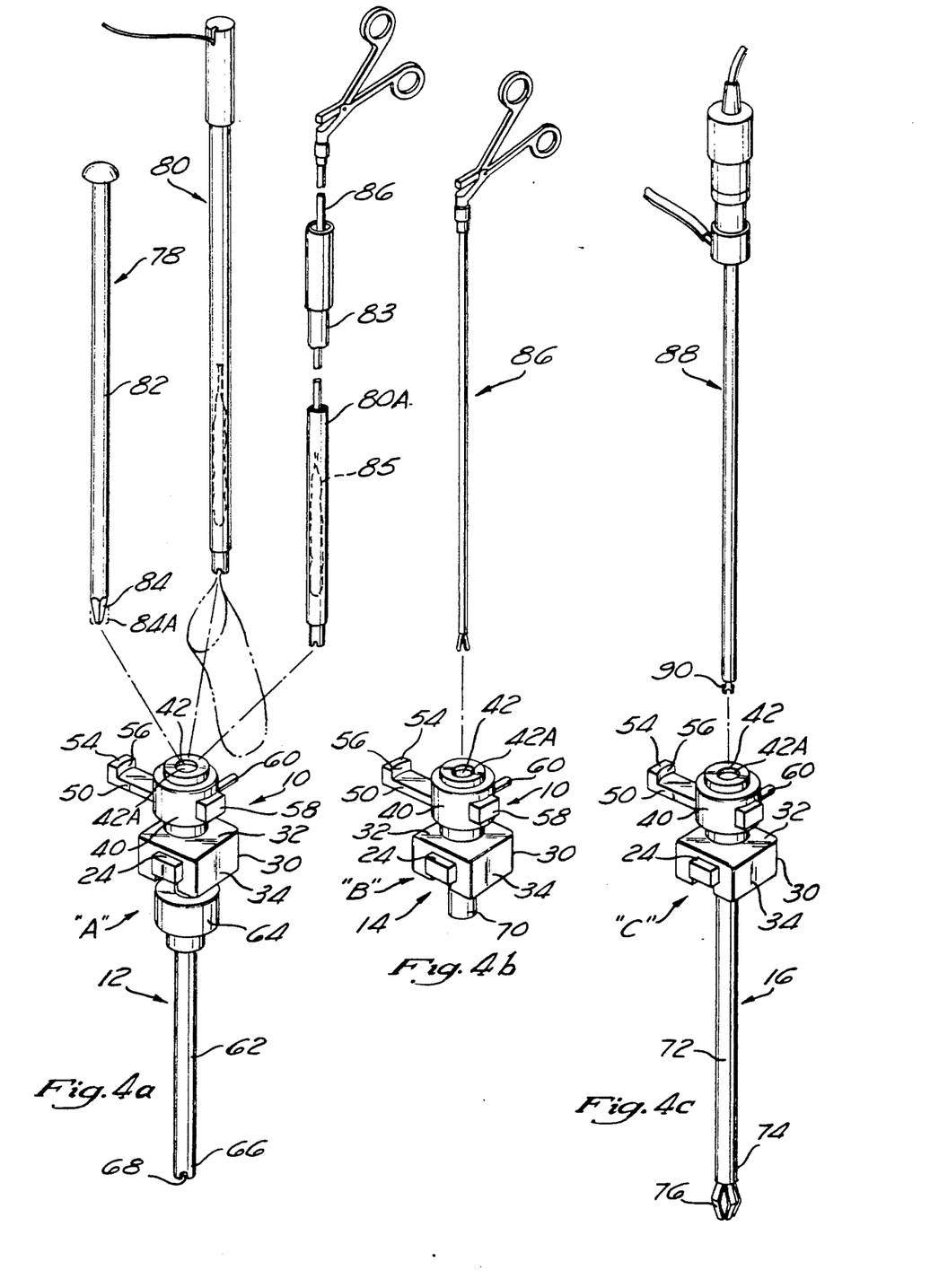

Referring now to FIGS. 4a, 4b and 4c, disclosed are devices which are preferably utilized in conjunction with a trocar device comprising the upper valving assembly 10 having a particular one of the three aforementioned trocar members attached thereto. As seen in FIG. 4a, a trocar device A comprising the upper valving assembly 10 and first trocar member 12 is preferably used in conjunction with a piercing stylet 78 and a containment bag introducing device 80. As can be appreciated, piercing stylet 78 and introducing device 80 may only be inserted into the trocar device A when the slide valve member 50 is actuated to the open position, thus causing the apertures 42, 52, 44, 28 and hollow lumen extending through the tubular sheath 62 to be coaxially aligned. Piercing stylet 78 comprises a shaft portion 82 which is sized such that the piercing tip 84 formed on the lower end thereof will extend beyond the distal tip 66 of tubular sheath 62 when the piercing stylet 78 is inserted into the trocar device A. The stylet is equipped with a protective shield 84A, which is automatically Withdrawn and exposes the piercing tip 84 when the tip contacts the skin at the access site. The containment bag introducing device 80 is fabricated in accordance with one of the embodiments disclosed in copending U.S. patent application Ser. No. 07/779,443 entitled "Method and System for Enclosing, Manipulating, Debulking and Removing Tissue Through Minimal Access Incisions". As such, the notch 68 formed in the distal tip 66 of tubular sheath 62 is used for purposes of maintaining the orientation of the rim member of the containment sac utilized in conjunction with the introducing device 80. As an alternative to the introducing device 80, an introducing device 80A wherein a forceps instrument 86 is inserted into a tubular sleeve 83 for selectively deploying containment sac 85 therefrom or drawing a portion of the sac 85 thereunto, may be utilized in conjunction with trocar device A. As will be recognized, a containment sac similar to those included with introducer devices 80, 80A may be inserted directly into the trocar device A.

As seen in FIG. 4b, a trocar device B comprising the upper valving assembly 10 and second trocar member 14 is preferably used in conjunction with the hand operable forceps instrument 86 which is insertable therethrough. Similar to the manner in which the piercing stylet 78 and introducing devices 80, 80A are inserted through the trocar device A, the forceps instrument 86 may only be inserted through the trocar device B when the upper valving assembly 10, and more particularly the slide valve member 50, is actuated to the open position. As seen in FIG. 4c, a trocar device C generally comprises the upper valving assembly 10 and the third trocar member 16. Trocar device C is preferably utilized in conjunction with a rotary debulking instrument 88 constructed in accordance with U.S. patent application Ser. No. 07/639,494 entitled "Method and Device for Intracorporeal Liquidization of Tissue And/Or Intracorporeal Fragmentation of Calculi During Endoscopic Surgical Procedures". As can be appreciated, because the trocar device C is utilized in conjunction with the rotary debulking instrument 88, the trocar member 16 used therewith includes the protective cage 76 disposed on the distal tip 74 of tubular sheath 72. As previously discussed with respect to trocar devices A and B, the slide valve member 50 of upper valve assembly 10 must be actuated to the open position before rotary debulking instrument 88 may be inserted through trocar device C. Importantly, tubular sheath 72 is sized in a manner wherein the cutting blade portion 90 of the debulking instrument 88 will be oriented within the opened protective cage 76 when debulking instrument 88 is inserted into trocar device C. Having thus described the various components comprising trocar devices A, B and C, as well as the various instruments utilized in conjunction therewith, a method for removing matter from a body cavity using the trocar devices A, B and C will now be described. Particularly, the following method will be described in relation to a cholecystectomy, though it will be recognized that the present invention may be utilized in conjunction with other surgical procedures.

Figure 5:
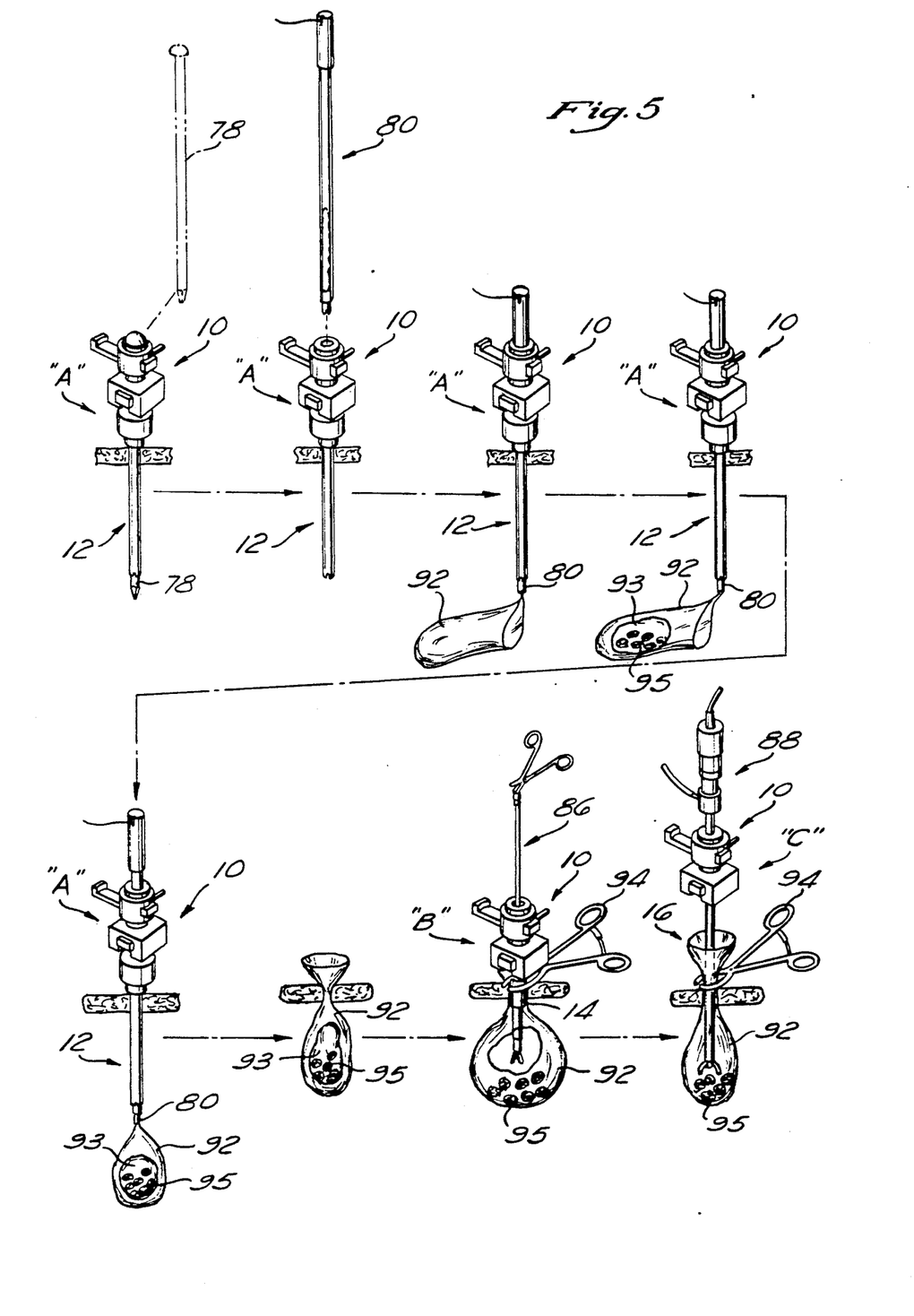
FIG. 5 is a step-by-step illustration of a method for removing matter from a body cavity using the device of the present invention.

Referring now to FIG. 5, after a patient has been anesthetized, an inflation needle is inserted into the abdomen and carbon dioxide is passed through the inflation needle into the peritoneum to create a distended pneumoperitoneum. The peritoneum is typically insufflated to a pressure of 14-18 mm Hg. Once the distended pneumoperitoneum has been established, the piercing/puncturing stylet 78 is inserted through the trocar device A. As previously indicated, the shaft portion 82 of the piercing stylet 78 is sized such that the piercing tip 84 extends slightly beyond the distal tip 66 of the sheath 62 of the trocar device A when the piercing stylet 78 is inserted therein. With the piercing stylet 78 so positioned, the trocar device A is grasped by the operator and inserted into the peritoneum. Upon entry into the peritoneum, a specific change in resistance or a "snap" is felt by the operator, indicating that the piercing/puncturing tip 84 of the stylet 78 has penetrated the peritoneal membrane. After the trocar device A has been so inserted, the piercing stylet 78 is withdrawn and removed from within trocar device A. Importantly, once the stylet 78 has been removed, the slide valve member 50 of upper valving assembly 10 is actuated to the closed position, therefore preventing the escape of gas from within the pneumoperitoneum. Additionally, a gas supply source is connected to the gas inlet port 60 and used to pressurize the containment sac. As will be recognized, the gas inlet port 60 communicates with the aperture 42 below the slide valve member 50 so that gas or liquid may pass from the supply source to the peritoneum when the slide valve member 50 is in the closed position.

With the trocar device A being partially inserted into the peritoneum, the slide valve member 50 is actuated to the open position and the containment bag introducing device 80 inserted through the trocar device A into the peritoneum. As previously specified, the upper valving assembly 10 includes sealing components disposed therein which the form the seal about introducing device 80 when such is inserted through trocar device A. Thus, though the slide valve member 50 is actuated to the open position to accommodate the introducing device 80, the pressure within the peritoneum is maintained. After the introducing device 80 has been inserted through the trocar device A, a containment sac 92 is deployed out of the distal end of the introducing device 80, 80A, and the aperture of the containment sac 92 is opened such that the desired organ, tissue or material, i.e. the gallbladder 93, may be inserted into the sao 92. Such insertion of the gallbladder 93 into the sac 92 may be carried out through the use of intracorporeally inserted instruments, under endoscopic visualization.

After the gallbladder 93 or other desired organ, tissue or material has been inserted into the containment sac 92 and has been incised and properly positioned, the containment sac 92 is partially withdrawn into the lumen of the introducing device 80 such that the aperture or opening of the sac 92 is completely or substantially within the lumen of the introducing device 80, 80A while the filled body of the sac 92 remains outward of the distal end of the introducing device 80, 80A. The introducing device 80, 80A and trocar device A are then simultaneously extracted from the opening or incision within the peritoneum thereby simultaneously withdrawing and upper portion of the containment sac 92. Thereafter, the trocar device A as well as the introducing device 80 may be separated from the sac 92, leaving the opening or aperture thereof in an exteriorized position, while the filled body of the sac 92 remains within the body cavity. After the upper portion of the containment sac 92 has been exteriorized, the introducing device 80, 80A is removed from within trocar device A and the slide valve member 50 is actuated to the closed position. Thereafter, the first trocar member 12 is detached from the upper valving assembly 10 and replaced with the second trocar member 14, thereby forming the second trocar device B. The trocar device B is then inserted into the containment sac 92 via the receipt of the tubular sheath 70 into the upper, exteriorized portion of the containment sac 92. A sealing instrument such as a pair of forceps with twin circular grips 94 is then clamped about the upper portion of the tubular sheath 70 thereby sealing the exteriorized portion of the containment sao 92 thereagainst. Importantly, the gas entering trocar device B via gas inlet port 60 passes into and inflates the containment sac 92. As will be recognized, such inflation of the containment sac 92 is necessary since the pressure within the peritoneum exceeds ambient pressure thereby causing the containment sac 92 to collapse against the material contained therewithin. After the containment sac 92 has been inflated, the slide valve member 50 is actuated to the open position and the forceps instrument 86 inserted through the trocar device B into the sac 92. In the cholecystectomy, the forceps instrument 86 may be utilized to incise the walls of the gallbladder 93 and remove the calculi 95 therefrom, during the removal process of the gallbladder. The gallbladder may be removed from sac 92 by forceps instrument 86 via trocar device B, with the calculi 95 remaining within sac 92. Another procedure to remove the gallbladder would be the following: First, remove trocar device B from containment sao 92. Then, using forceps instrument 86, grasp the neck of the gallbladder and pull the gallbladder through the incision. The pressure of the surrounding incision on the walls of the gallbladder will force or squeeze the contents of the gallbladder out of the incised opening of the gallbladder.

After the calculi 95 have been removed from gallbladder 93, the forceps instrument 86 is removed from within the trocar device B. Thereafter, the slide valve member 50 is actuated to the closed position, the sealing device 94 is removed from the tubular sheath 70, and the trocar device B is removed from within the containment sac 92. The second trocar member 14 is then removed from the upper valving assembly 10 and replaced with the third trocar member 16, thus forming the third trocar device C. Third trocar device C is then inserted into the exteriorized portion of the containment sac 92 via the receipt of the distal tip 74 and protective cage 76 of tubular sheath 72 thereinto. Inlet port 60 is operable to re-inflate the containment sac 92 which once again collapses about the calculi 95 upon the removal of the trocar device B therefrom. The inflation of the sac will be with liquid to enhance the grinding process. After the trocar device C is inserted into the containment sac 92, the sealing device 94 is clamped about the tubular sheath 72 thereby sealing the exteriorized portion of the containment sac 92 thereagainst to prevent leakage between containment sac 92 and tubular sheath 72.

After the containment sac 92 has been sealed against the tubular sheath 72, the slide valve member 50 is actuated to the open position, and the rotary debulking instrument 88 is inserted through the trocar device C. The rotary debulking instrument 88 is then used for debulking, crushing, morcellizing, grinding, mulching or otherwise treating the organ, tissue or material, i.e. the calculi 95, within the sao 92. Importantly, the protective cage 76 disposed on the distal tip 74 of tubular sheath 72 is adapted to prevent the cutting blade portion 90 of debulking instrument 88 from piercing the containment sac 92. After any desired debulking, crushing, liquidizing, grinding, mulching or other treatment of the sac contents has been completed, the contents of the sac 92 may be fully or partially aspirated or removed therefrom. In this respect, after the debulking instrument 88 has been utilized, the resulting slurry is removed from the containment sao 92 via suction through port 60. As will be recognized, in order to create a wide channel for the slurry, the debulking assembly 88 must first be withdrawn from within the sac 92. Suction can be created only if the slide member 50 valve V is pushed to the closed position. Advantageously, removing the slurry from the sac 92 renders the body of the sao 92 sufficiently collapsible or compressible to be pulled through the small body opening or incision after the trocar device C has been removed from the sac 92.

Figures 6A, 6B, 6C, 7A, 7B, 7C, 8:
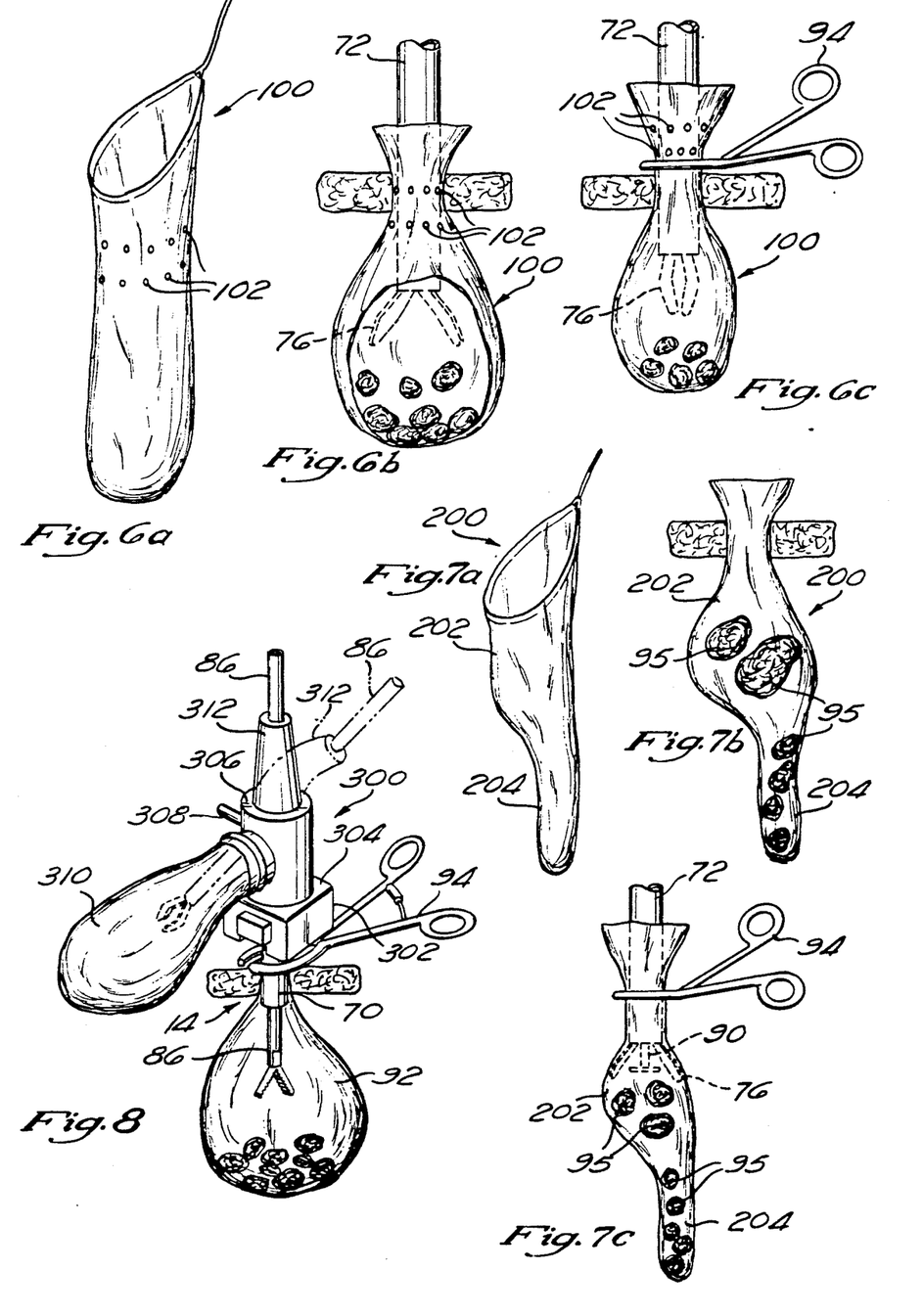
FIG. 6a is a perspective showing of an alternative embodiment of a containment bag usable in the present invention and having a plurality of pressure-equalizing perforations formed therein.
FIG. 6b is an elevational showing of the containment sac of FIG. 6a partially inserted into a body cavity in a first pressure-equalized position.
FIG. 6c is an elevational showing of the containment sac of FIG. 6a partially inserted into a body cavity in a second non-pressure equalized position.
FIG. 7a is a second alternative embodiment of a containment sac of the present invention which is specifically configured to separate matter passable through a minimal access incision from matter which is not passable through such minimal access incision.
FIG. 7b is an elevational view of the containment sac of FIG. 6a partially disposed within a body cavity and having large and small masses of material disposed therein.
FIG. 7c is elevational view of the containment sac of FIG. 6a partially disposed within a body cavity and having large and small masses of material disposed therein and inserted thereinto an instrument for debulking the matter which is too large to pass through the minimal access incision.
FIG. 8 is a perspective view of an alternative embodiment of the device of the present invention wherein the upper valving assembly is provided with an exteriorized side containment bag and a flexible boot for permitting instrument mediated manipulation and passage of material from an intracorporeal containment sao to the exteriorized side containment sac.

Referring now to FIGS. 6a, 6b and 6c, as previously specified, the pressure within the peritoneum of 14–16 mm Hg causes the containment sac 92 to collapse about the tissue, material or organ disposed therewithin when the trocar device A is removed from within the sac 92. In order to prevent the collapse of the sac 92 from occurring, there is provided a containment sac 100 for incorporation into the introducing device 80, 80A. Advantageously, containment sac 100 includes two rings of apertures 102 disposed within the upper portion thereof, with each of the apertures 102 comprising the upper and lower rings being in substantial vertical alignment. Importantly, when the containment sac 100 is disposed within the peritoneum with only the upper portion being exteriorized, at least one ring of apertures 102 will also be disposed within the insufflated peritoneum. As will be recognized, the inclusion the apertures 102 within the sao 100 allows the pressure to equilibrate between the peritoneum and the interior of the sac 100, thereby preventing the collapse of the sac 100 against the material disposed therein. When the pressure has been equalized, an instrument such as the third trocar device C may be inserted into the interior of the sac 100, with the protective cage 76 disposed on the distal tip 74 of tubular sheath 72 being able to actuate to an extended position due to the lack of pressure being exerted thereagainst by the sac 100. If required, the second trocar device B may also be inserted into sao 100 and the contents of the sac manipulated.

As seen in FIG. 6c, before the debulking instrument 88 is inserted into the trocar device C, and prior to the sealing of the upper, exteriorized portion of the sac 100 against the tubular sheath 72 via the sealing device 94, the upper portion of the sac 100 may be pulled through the incision such that both rings of apertures 102 are exteriorized. Importantly, the exteriorization of the apertures 102 is necessary prior to the debulking, liquidizing, grinding, etc. of the material within the sac 100 through the utilization of the debulking instrument 88 so that no liquidized matter will escape from the containment sac 100 via the apertures 102. It will be recognized, that the containment sao 100 previously shown and described may be utilized in conjunction with the introducer device described in parent application Ser. No. 07/779,443 filed Oct. 18, 1991.

Referring now to FIGS. 7a, 7b and 7c, disclosed is a containment sao 200 which may also be utilized in conjunction with introducing device 80, 80A as an alternative to the containment sac 92 included therewith. Importantly, certain tissues, materials or organs within the containment sac of the introducer device 80, 80A, such as calculi 95 may be sized so as to be removable from the peritoneum via the incision without the need for the liquidization, grinding or debulking thereof. As such, containment sac 200 is specifically configured to allow reduced size material placed therewithin to fall to a region wherein no debulking, grinding or liquidization thereof via the rotary debulking instrument 88 will occur. In this respect, containment sac 200 includes a large diameter upper portion 202 and a small diameter lower portion 204. As seen in FIG. 7b, the calculi 95 or other materials, tissues or organs introduced into the sac 200 having a smaller size will fall into the lower portion 204 when the bag is exteriorized, while larger matter will remain in the upper portion 202. Such separation of the stones will prevent clustering of a large number of small stones at the incision site when the sac is pulled against the incision. The cluster could be so large that it would make withdrawal impossible. As seen in FIG. 7c, when the trocar device C is inserted into the exteriorized portion of the containment sac 200 and the rotary debulking instrument 88 inserted therethrough, the cutting blade portion 90 of the debulking instrument 88 will only grind, debulk or liquidize the larger material contained within the upper portion 202 of containment sac 200. The smaller material disposed within the lower portion 204 is removed through the incision when the sac 200 is pulled therethrough. It will be recognized that the containment sao 200 may also include apertures as disclosed with respect to containment sac 100. Additionally, containment sac 200 may also be utilized in conjunction with the introducer device disclosed in parent application Ser. No. 07/779,443 filed Oct. 18, 1991. As can be appreciated, limiting the debulking to the large size stones makes the debulking process more effective. During morcellization, removed tissue fragments will settle into the lower portion 204 of the sac 200, thereby increasing the efficiency of the morcellization.

It is contemplated that the lower portion 204 of sac 200 may be made of different material than the upper portion 202. In this respect, the lower portion 204 is preferably fabricated from materials adapted to withstand high pulling forces and not bulge or deteriorate from its cylindrical shape during withdrawal. Additionally, the material should be of high tensile strength and may be formed from polyamide, polypropylene, or polyurethane. High tensile strength may also be achieved by reinforcing the lower section 204 with net-like material (e.g. a grid of plastic fibers or plastic strips) embedded into the material or juxtapositioned between adjacent layers of the material.

Referring now to FIG. 8, disclosed is an upper valving assembly 300 which may be utilized in the present invention as an alternative to the upper valving assembly 10 previously shown and described. Upper valving assembly 300 includes a housing 302 identically configured to the housing 30 previously described with respect to upper valving assembly 10. As such, housing 302 includes a T-shaped slot extending therethrough which is identically configured to the T-shaped slot 36. Extending upwardly from the upper surface 304 of housing 302 is a secondary cylindrical housing 306 having a gas/liquid inlet port 308 extending therefrom. Additionally, attached to the outer surface of cylindrical housing 306 is a secondary containment sac 310 which communicates with the interior of the housing 308 via a sac port 311 Extending upwardly from the top surface of housing 306 is a flexible extension 312.

Importantly, the upper valving assembly 300 is adapted to be utilized primarily in conjunction with the second trocar member 14 and the forceps instrument 86. In this respect, after the upper portion of the containment sac 92 has been exteriorized and the tubular sheath 70 of second trocar member 14 inserted thereinto, materials, tissues or organs disposed within the containment sac 92 may be passed from therewithin to the interior of the containment sao 310 via the lumen of the tubular sheath 70, the interior of the housing 304, the interior of the housing 306 and the sac port 311. As will be recognized, such transfer of material within the containment sac 92 into the containment sac 310 occurs without the material being subject to contamination. During the manipulation, the pressure seal created between forceps instrument 86 and flexible extension 312 prevents a loss of pressure in the system. Advantageously, the forceps instrument 86 may be manipulated so as to transfer material from the sac 92 into the sac 310 via the selective bending of the flexible extension 312 attached to the housing 306. This device can also be operated without the sac 92 to remove tissue directly from the abdomen into the storage sac 310.

The above-described methodology is but one example of an operative procedure that may be carried out using a device of the present invention. It will be appreciated that other embodiments of the invention may be employed in other procedures, all of which are within the intended scope of the present application.

The present invention has been described herein with reference to presently preferred embodiments of the device and with reference to specific examples of methods of utilizing the device. The foregoing description of the preferred embodiments and examples of the method are not intended to limit the invention in any way. In fact, by applying current or future knowledge, those skilled in the art will recognize numerous modifications, substitutions, deletions or alterations which may be made to the above-described preferred embodiments and examples without departing from the spirit and scope of the present invention. It is intended that all such modifications, substitutions, deletions or alterations be included within the scope of the following claims and the equivalents thereof.

What is claimed is:

1. A system for facilitating passage of instruments into a body cavity, said device comprising:
   a. an upper valving assembly having a rigid body, a hollow bore extending vertically therethrough and an elastomeric valving diaphragm positioned transversely across said hollow bore and having at least one slit opening therein to permit passage of elongate instruments therethrough;
   b. a plurality of lower trocar members alternately and interchangeably connectable to said upper valving assembly, each said lower trocar member having a hollow lumen extending longitudinally therethrough, said plurality of interchangeable lower trocar members comprising:
      i. A first lower trocar member having a length of 0.5-3 inches;
      ii. a second lower trocar member having a length greater than 3 inches, and
      iii. a third lower trocar member having a protective cage formed on the distal tip thereof.

2. The device of claim 1 further in combination with:
a piercing stylet insertable through said upper valving assembly and through said second lower trocar member.

3. The device of claim 1 further in combination with:
a surgical tissue containment sac insertable trough said upper valving assembly and through said second lower trocar member.

4. The device of claim 1 further in combination wit a forceps/grasper instrument insertable through said upper valving assembly and through said second lower trocar member.

5. The device of claim 1 further in combination with a forceps/grasper instrument insertable through said upper valving assembly and through said first lower trocar member.

6. The device of claim 1 further in combination with a rotary morcelling instrument insertable through said upper valving assembly and through said lower trocar member having said protective cage disposed at the distal tip thereof.

7. The device of claim 1 further comprising a slide valve positioned in said upper valving assembly for alternatively opening and closing the bore of said upper valving assembly.

* * * * *

UNITED STATES PATENT AND TRADEMARK OFFICE
CERTIFICATE OF CORRECTION

PATENT NO. : 5,224,930
DATED : July 6, 1993
INVENTOR(S) : Edmund E. Spaeth, Alexander S. Borsanyi, Alex Bowie, John T. Sorensen It is certified that error appears in the above-identified patent and that said Letters Patent is hereby corrected as shown below:

On the Title Page, Item [57], line 8; after after the number 0.5-, delete "0.3" and substitute therefore --3.0--.

Column 7, Line 33, delete "Withdrawn" and substitute therefore --withdrawn--.

Column 9, Line 6 delete "sao" and substitute therefore --sac--.

Column 9, Line 59, delete "sao" and substitute therefore --sac--.

Column 10, Line 28, delete "sao" and substitute therefore --sac--.

Column 10, Line 44, delete "sao" and substitute therefore --sac--.

Column 10, Line 65, delete "sao" and substitute therefore --sac--.

Signed and Sealed this

Tenth Day of May, 1994

*Attest:*

BRUCE LEHMAN

*Attesting Officer*     Commissioner of Patents and Trademarks